United States Patent
Adler et al.

(10) Patent No.: US 12,029,606 B2
(45) Date of Patent: Jul. 9, 2024

(54) ELECTRONIC STETHOSCOPE WITH ENHANCED FEATURES

(71) Applicant: BAT CALL D. ADLER LTD., Nesher (IL)

(72) Inventors: Doron Adler, Haifa (IL); Igor Kagan, Kiriat Bialik (IL); Ezra Salomon, Rakefet (IL); Omri Adler, Haifa (IL); David Linhard, Haifa (IL)

(73) Assignee: SANOLLA LTD., Nesher (IL)

( * ) Notice: Subject to any disclaimer, the term of this patent is extended or adjusted under 35 U.S.C. 154(b) by 1044 days.

(21) Appl. No.: 16/636,649

(22) PCT Filed: Aug. 22, 2018

(86) PCT No.: PCT/IB2018/056335
§ 371 (c)(1),
(2) Date: Feb. 5, 2020

(87) PCT Pub. No.: WO2019/048960
PCT Pub. Date: Mar. 14, 2019

(65) Prior Publication Data
US 2021/0145398 A1    May 20, 2021

Related U.S. Application Data

(63) Continuation-in-part of application No. 15/953,502, filed on Apr. 16, 2018, now Pat. No. 11,116,478.
(Continued)

(51) Int. Cl.
*A61B 7/04*    (2006.01)
*A61B 5/00*    (2006.01)
(Continued)

(52) U.S. Cl.
CPC ............ *A61B 7/04* (2013.01); *A61B 5/14551* (2013.01); *A61B 5/742* (2013.01); *A61B 7/003* (2013.01); *H04R 1/46* (2013.01)

(58) Field of Classification Search
CPC .. A61B 7/04; A61B 7/003; H04R 1/46; G06F 17/14
See application file for complete search history.

(56) References Cited

U.S. PATENT DOCUMENTS

| 872,448 A | 12/1907 | Penhallow |
| 3,433,959 A | 3/1969 | Atwood et al. |

(Continued)

FOREIGN PATENT DOCUMENTS

| CN | 103479385 A | 1/2014 |
| CN | 103479386 A | 1/2014 |

(Continued)

OTHER PUBLICATIONS

Cision PR Newswire, "Bat-Call's Revolutionary AI Based Infra-Sound Auscultation Technology to Fight Covid-19", pp. 1-4, Apr. 1, 2020, as downloaded from https://www.prnewswire.com/news-releases/bat-calls-revolutionary-ai-based-infra-sound-auscultation-technology-to-fight-covid-19-301033267.html.
(Continued)

*Primary Examiner* — Carrie R Dorna
*Assistant Examiner* — Karen E Toth
(74) *Attorney, Agent, or Firm* — KLIGLER & ASSOCIATES PATENT ATTORNEYS LTD.

(57) ABSTRACT

A medical device (20) includes a case (32), having a front surface that is configured to be brought into contact with a body of the living subject (24). A microphone (34) is contained in the case and configured to sense acoustic waves emitted from the body and to output an acoustic signal in response thereto. A proximity sensor (56) is configured to
(Continued)

output a proximity signal indicative of contact between the front surface and the body. At least one speaker (49) is configured to output audible sounds. Processing circuitry (50) is coupled to detect, in response to the proximity signal, that the front surface is in contact with the body, and in response to the detected contact, to process the acoustic signal so as to generate an audio output and to convey the audio output to the at least one speaker.

28 Claims, 5 Drawing Sheets

Related U.S. Application Data

(60) Provisional application No. 62/554,041, filed on Sep. 5, 2017.

(51) Int. Cl.
*A61B 5/1455* (2006.01)
*A61B 7/00* (2006.01)
*H04R 1/46* (2006.01)

(56) References Cited

U.S. PATENT DOCUMENTS

| | | | |
|---|---|---|---|
| 3,580,082 A | 5/1971 | Strack et al. | |
| 4,792,145 A | 12/1988 | Eisenberg et al. | |
| 5,031,637 A | 7/1991 | Parra | |
| 5,301,679 A | 4/1994 | Taylor | |
| 5,853,005 A | 12/1998 | Scanlon | |
| 6,050,950 A * | 4/2000 | Mohler | A61B 7/00 |
| | | | 600/528 |
| 6,154,551 A | 11/2000 | Frenkel | |
| 6,520,924 B2 | 2/2003 | Lee | |
| 6,699,204 B1 | 3/2004 | Kehyayan et al. | |
| 6,778,673 B1 | 8/2004 | Hobelsberger | |
| 6,788,417 B1 | 9/2004 | Zumberge et al. | |
| 6,887,208 B2 | 5/2005 | Kushnir et al. | |
| D526,320 S | 8/2006 | Brandon et al. | |
| 7,458,939 B2 | 12/2008 | Munk | |
| 7,520,861 B2 | 4/2009 | Murphy | |
| 7,976,480 B2 | 7/2011 | Grajales et al. | |
| 8,015,878 B2 | 9/2011 | Melikechi et al. | |
| D659,840 S | 5/2012 | Cheng et al. | |
| D673,678 S | 1/2013 | Hong | |
| 8,419,652 B2 | 4/2013 | Rajamani et al. | |
| 8,475,396 B2 | 7/2013 | Jones et al. | |
| D711,532 S | 8/2014 | Habboushe et al. | |
| 8,920,343 B2 * | 12/2014 | Sabatino | A61B 5/742 |
| | | | 381/67 |
| 9,101,274 B2 | 8/2015 | Bakema et al. | |
| 9,138,257 B2 | 9/2015 | Revivo | |
| 9,208,287 B2 | 12/2015 | Waterson et al. | |
| 9,277,330 B2 | 3/2016 | Aharoni et al. | |
| 9,345,432 B2 | 5/2016 | Salisbury et al. | |
| D767,770 S | 9/2016 | Purfey | |
| 9,445,779 B2 | 9/2016 | Shams et al. | |
| D794,201 S | 8/2017 | Newhouse et al. | |
| 9,867,591 B2 | 1/2018 | Shams et al. | |
| 10,092,269 B2 | 10/2018 | Shams et al. | |
| 10,141,007 B1 * | 11/2018 | Kim | G10L 25/18 |
| D865,167 S | 10/2019 | Kirgizov | |
| D880,710 S | 4/2020 | Amoyal | |
| 10,709,353 B1 | 7/2020 | McLane | |
| 10,842,416 B2 | 11/2020 | Joseph et al. | |
| 10,881,330 B2 | 1/2021 | Joseph et al. | |
| D950,748 S | 5/2022 | Gong | |
| 2001/0030077 A1 * | 10/2001 | Watson | A61B 5/742 |
| | | | 381/67 |
| 2002/0071570 A1 | 6/2002 | Cohen et al. | |
| 2002/0183642 A1 | 12/2002 | Murphy | |
| 2003/0002685 A1 | 1/2003 | Werblud | |
| 2004/0260193 A1 * | 12/2004 | LaSala | A61B 7/04 |
| | | | 600/528 |
| 2005/0222515 A1 | 10/2005 | Polyshchuk et al. | |
| 2005/0273015 A1 | 12/2005 | Bauer et al. | |
| 2006/0070623 A1 | 4/2006 | Wilkinson et al. | |
| 2007/0050715 A1 | 3/2007 | Behar | |
| 2007/0058818 A1 | 3/2007 | Yoshimine | |
| 2008/0013747 A1 | 1/2008 | Tran | |
| 2009/0171231 A1 | 7/2009 | Caro et al. | |
| 2009/0232322 A1 * | 9/2009 | Tseng | A61B 7/04 |
| | | | 381/67 |
| 2009/0316925 A1 * | 12/2009 | Eisenfeld | H04R 1/46 |
| | | | 381/67 |
| 2010/0298740 A1 | 6/2010 | Gelman et al. | |
| 2011/0137209 A1 | 6/2011 | Lahiji et al. | |
| 2011/0222697 A1 | 9/2011 | Dong et al. | |
| 2011/0224988 A1 | 9/2011 | Mahajan et al. | |
| 2012/0143018 A1 | 6/2012 | Skidmore et al. | |
| 2012/0209131 A1 | 8/2012 | Jones et al. | |
| 2013/0041278 A1 | 2/2013 | Bai et al. | |
| 2013/0060100 A1 | 3/2013 | Wurm et al. | |
| 2014/0073864 A1 | 3/2014 | Engelbrecht et al. | |
| 2014/0155762 A1 | 6/2014 | Maskara et al. | |
| 2014/0290372 A1 | 10/2014 | Lagakos et al. | |
| 2014/0327775 A1 * | 11/2014 | Cho | H04N 23/62 |
| | | | 348/148 |
| 2015/0073306 A1 | 3/2015 | Abeyratne et al. | |
| 2015/0119758 A1 | 4/2015 | Rogers et al. | |
| 2015/0327775 A1 * | 11/2015 | Carter | A61B 5/14551 |
| | | | 600/301 |
| 2016/0007923 A1 * | 1/2016 | Yamamoto | A61B 5/7445 |
| | | | 600/586 |
| 2016/0050506 A1 * | 2/2016 | Kim | H04R 1/245 |
| | | | 381/56 |
| 2016/0095571 A1 * | 4/2016 | Shams | A61B 5/02411 |
| | | | 600/586 |
| 2016/0306940 A1 | 10/2016 | Farhoud | |
| 2017/0079612 A1 | 3/2017 | Park | |
| 2017/0156632 A1 * | 6/2017 | Swiston | A61B 5/073 |
| 2017/0273580 A1 | 9/2017 | Lee | |
| 2018/0115839 A1 | 4/2018 | Eichfeld et al. | |
| 2018/0228468 A1 | 8/2018 | Adler et al. | |
| 2019/0000413 A1 * | 1/2019 | Adler | H04R 1/406 |
| 2019/0076129 A1 | 3/2019 | Ward, III et al. | |
| 2019/0099156 A1 | 4/2019 | Bocca et al. | |
| 2019/0125270 A1 | 5/2019 | Deriso | |
| 2019/0298183 A1 | 10/2019 | Burg et al. | |
| 2020/0060641 A1 | 2/2020 | Shekhar et al. | |
| 2020/0253480 A1 | 8/2020 | Hall et al. | |
| 2020/0368090 A1 | 11/2020 | Waterson et al. | |
| 2021/0345939 A1 | 11/2021 | Jumbe et al. | |
| 2023/0142937 A1 | 5/2023 | Jha et al. | |

FOREIGN PATENT DOCUMENTS

| | | |
|---|---|---|
| CN | 203506748 U | 4/2014 |
| CN | 107510473 A | 12/2017 |
| CN | 306290265 | 1/2021 |
| DE | 202005006661 U1 | 8/2005 |
| JP | D1561413 | 10/2016 |
| JP | D1717812 | 6/2022 |
| KR | 20120040530 A | 4/2012 |
| WO | 9325874 A1 | 12/1993 |
| WO | 0002486 A1 | 1/2000 |
| WO | 2002009586 A2 | 2/2002 |
| WO | 2006075263 A1 | 7/2006 |
| WO | 2011117862 A2 | 9/2011 |
| WO | 2014163443 A1 | 10/2014 |
| WO | 2015157458 A1 | 10/2015 |
| WO | 2016113562 A1 | 7/2016 |
| WO | 2017141165 A1 | 8/2017 |

OTHER PUBLICATIONS

International Application # PCT/IB2021/058755 Search Report dated Jan. 5, 2022.

(56) References Cited

OTHER PUBLICATIONS

International Application # PCT/IB2021/059711 Search Report dated Feb. 3, 2022.
International Application # PCT/IB2021/059710 Search Report dated Feb. 10, 2022.
European Application # 20168052.7 Search Report dated Jun. 29, 2020.
U.S. Appl. No. 15/953,502 Office Action dated Sep. 11, 2020.
EP Application # 18853978.7 Search Report dated Apr. 22, 2021.
EP Application # 18855091.7 Search Report dated Apr. 22, 2021.
Huang et al., "The Respiratory Sound Features of COVID-19 Patients Fill Gaps Between Clinical Data and Screening Methods," medRxiv, Preprint, pp. 1-12, Apr. 10, 2020, as downloaded from https://www.medrxiv.org/content/10.1101/2020.04.07.20051060v1.
U.S. Appl. No. 17/138,986 Office Action dated Sep. 15, 2022.
U.S. Appl. No. 15/953,502 Office Action dated Feb. 19, 2021.
Amazon, "Thinklabs One Digital Stethoscope", pp. 1-9, Jan. 6, 2019 downloaded from www.amazon.com/Thinklabs-One-Digital-Stethoscope/dp/B07BRQRNW7.
Bat-Call, "CompuSteth", pp. 1-3, Mar. 23, 2019 downloaded from https://bat-call.com/products/compusteth/.
Padmanabhan et al., "Accelerometer type cardiac transducer for detection of low-level heart sounds", IEEE Transactions on Biomedical Engineering, vol. 40, No. 1, pp. 21-28, Jan. 1, 1993.
Bukhman et al., "Spectral analysis of acoustic vibrations on the surface of the human body," Acoustical Physics, vol. 41, Issue 1, pp. 1-10, year 1995.
International Application # PCT/IB2018/056335 search report dated Dec. 26, 2018.
U.S. Appl. No. 17/138,986 Office Action dated Mar. 21, 2023.
EP Application # 18855091.7 Office Action dated Mar. 15, 2023.
U.S. Appl. No. 29/794,958 Office Action dated Oct. 5, 2023.
Rudolf Riester GMBH, "PyXy + AI=New Health Surveillance System," pp. 1-6, year 2023, as downloaded from https://pyxy.ai/technolgy.
JM Science, "Electronic Stethoscope," Product Information, pp. 1-4 year 2023, as downloaded from https://imscience.com/products/electronic-stethoscope-mitorika.
Mesko, "Playback Heart Sounds: The eKuore Pro Digital Stethoscope—Review," pp. 1-7, year 2019.

* cited by examiner

ELECTRONIC STETHOSCOPE WITH ENHANCED FEATURES

CROSS-REFERENCE TO RELATED APPLICATIONS

This application claims the benefit of U.S. Provisional Patent Application 62/554,041, filed Sep. 5, 2017. This application is also a continuation in part of U.S. patent application Ser. No. 15/953,502, filed Apr. 16, 2018. Both of these related applications are incorporated herein by reference.

FIELD OF THE INVENTION

The present invention relates generally to methods, apparatus and software for medical diagnosis, and particularly to electronic stethoscopes and methods for their use.

BACKGROUND

Auscultation has been a key technique in medical diagnosis for centuries. In auscultation, the medical practitioner listens to the internal sounds of the body, typically using a stethoscope. Auscultation is most commonly performed for the purpose of examining the circulatory and respiratory systems, and thus diagnosing conditions of the heart and lungs in particular. In more recent years, electronic stethoscopes and methods of digital processing of body sounds have become available, in order to enhance and supplement the practitioner's auditory capabilities.

For example, U.S. Pat. No. 5,853,005 describes an acoustic monitoring system in which a transducer in communication with fluid in a pad is held in close contact against a sound or movement source and monitors acoustic signals transferred into the fluid. The signal pattern is monitored aurally and/or compared to predetermined reference patterns.

As another example, U.S. Pat. No. 6,699,204 describes a device for analyzing auscultation sounds, in particular respiratory sounds. The device comprises an input receiving a sound signal sampled in intensity levels each associated with a selected time, and storage means comprising a processing module for evaluating, in cooperation with computing means, a set of transformed intensity levels, each associated with a predetermined sound frequency. It further comprises an output connected to the storage means for delivering each transformed intensity level in correspondence with an associated frequency, and means for representing intensity levels transformed on the basis of frequencies, to obtain a spectral representation of the auscultation sound.

U.S. Patent Application Publication 2005/0222515 describes methods of analyzing patient's heart, using a cardiovascular sound signature in diagnosis at the early stages of cardiac dysfunctions. The invention is said to present cardiovascular sounds in time and frequency while keeping signal resolution equally strong in both directions.

PCT International Publication WO 2017/141165, whose disclosure is incorporated herein by reference, describes apparatus for detecting sound waves emanating from a body of a subject. The apparatus includes a housing and a membrane, disposed at an opening of the housing. The membrane is configured to deflect, when an outer face of the membrane contacts the body, responsively to the sound waves impinging on the membrane. The apparatus further includes a piezoelectric microphone, disposed within the housing, configured to detect vibrations of air caused by the deflection of the membrane, and to generate a microphone output in response thereto. An accelerometer, disposed on an inner face of the membrane, deflects, along with the membrane, at frequencies below a minimum frequency that is detectable by the piezoelectric microphone, and generate an accelerometer output in response thereto. A processor processes the microphone output and the accelerometer output, and generates, responsively to the processing, a sound signal that represents the impinging sound waves.

SUMMARY

Embodiments of the present invention that are described hereinbelow provide apparatus and methods for collecting, processing and analyzing signals from the body surface.

There is therefore provided, in accordance with an embodiment of the invention, a medical device, which includes a case, having a front surface that is configured to be brought into contact with a body of the living subject. A microphone is contained in the case and configured to sense acoustic waves emitted from the body and to output an acoustic signal in response thereto. A proximity sensor is configured to output a proximity signal indicative of contact between the front surface and the body. At least one speaker is configured to output audible sounds. Processing circuitry is coupled to detect, in response to the proximity signal, that the front surface is in contact with the body, and in response to the detected contact, to process the acoustic signal so as to generate an audio output and to convey the audio output to the at least one speaker.

In some embodiments, the device includes a motion sensor, which is contained in the case and is configured to output a motion signal in response to motion of the front surface. The processing circuitry can be configured to process the motion signal in order to detect a respiratory cycle of the subject. In a disclosed embodiment, the front surface includes a membrane, which is configured to vibrate in response to the acoustic waves emitted from the body, and the motion sensor is configured to sense the motion of the membrane, and the processing circuitry is configured to process the motion signal in order to detect an infrasonic component of the acoustic waves.

In one embodiment, the processing circuitry is configured to process the acoustic signal so as to generate a frequency-stretched audio output in which infrasonic frequency components of the acoustic signal are shifted to audible frequencies while preserving the periodicity of the periodic physiological activity, and to convey the frequency-stretched audio output to the at least one speaker.

Additionally or alternatively, the processing circuitry is configured to power down one or more components of the device when the proximity signal indicates that the front surface is not in contact with the body, and to power up the one or more components when the proximity signal indicates that contact has been made between the front surface and the body.

In some embodiments, the device includes a pair of earphones, which are configured to be inserted in respective ears of an operator of the device and to convey the audible sounds to the ears. In one such embodiment, the processing circuitry is configured to detect that the earphones have been spread apart and to power up one or more components of the device in response thereto.

Additionally or alternatively, the processing circuitry is configured to detect, in response to the proximity signal, a quality of the contact between the front surface and the body, and to output an indication of the detected quality to an operator of the device.

In some embodiments, the proximity sensor includes at least one emitter, which is configured to emit optical radiation toward the body, and a detector, which is configured to sense the optical radiation reflected from the body. In one such embodiment, the at least one emitter is configured to emit infrared radiation, and the processing circuitry is configured to measure a level of oxygen saturation in blood of the subject responsively to the reflected radiation sensed by the detector.

Typically, the case has a rear surface opposite the front surface, and the device includes a touch-sensitive display screen mounted on the rear surface of the case. In some embodiments, the processing circuitry is configured to present a user interface on the display screen and to receive an input from an operator of the device via the display screen indicating a processing mode and frequency shift to be applied in processing of the acoustic signal. The processing mode can be selected from a group of processing modes consisting of a cardiac signal processing mode and a respiratory signal processing mode.

Additionally or alternatively, the processing circuitry is configured to compute, responsively to the acoustic signal, and render to the display screen an acoustic signature, including a graphical representation of a spectral distribution of an energy of the acoustic waves over a period of physiological activity. In one embodiment, the processing circuitry is configured to compute respective autocorrelations of the acoustic signal for a plurality of different times within a period of the physiological activity, to transform the respective autocorrelations to a frequency domain, and to render the acoustic signature to the display screen responsively to the transformed autocorrelations. In some embodiments, the acoustic waves include an infrasonic component, and the spectral distribution includes the energy at infrasonic frequencies. In a disclosed embodiment, the graphical representation includes a plot having a frequency axis and a time axis defining a time-frequency plane and presenting a value of the energy at each point in the time-frequency plane.

There is also provided, in accordance with an embodiment of the invention, a method for medical diagnosis, which includes receiving, from a microphone in a case having a front surface that is brought into contact with a body of a living subject, an acoustic signal in response to acoustic waves emitted from the body. A proximity signal is indicative of contact between the front surface of the case and the body. In response to the proximity signal, contact of the front surface with the body is detected. In response to the detected contact, the acoustic signal is processed so as to generate and convey an audio output to at least one speaker.

The present invention will be more fully understood from the following detailed description of the embodiments thereof, taken together with the drawings in which:

DETAILED DESCRIPTION OF EMBODIMENTS

Overview

Figure 1:
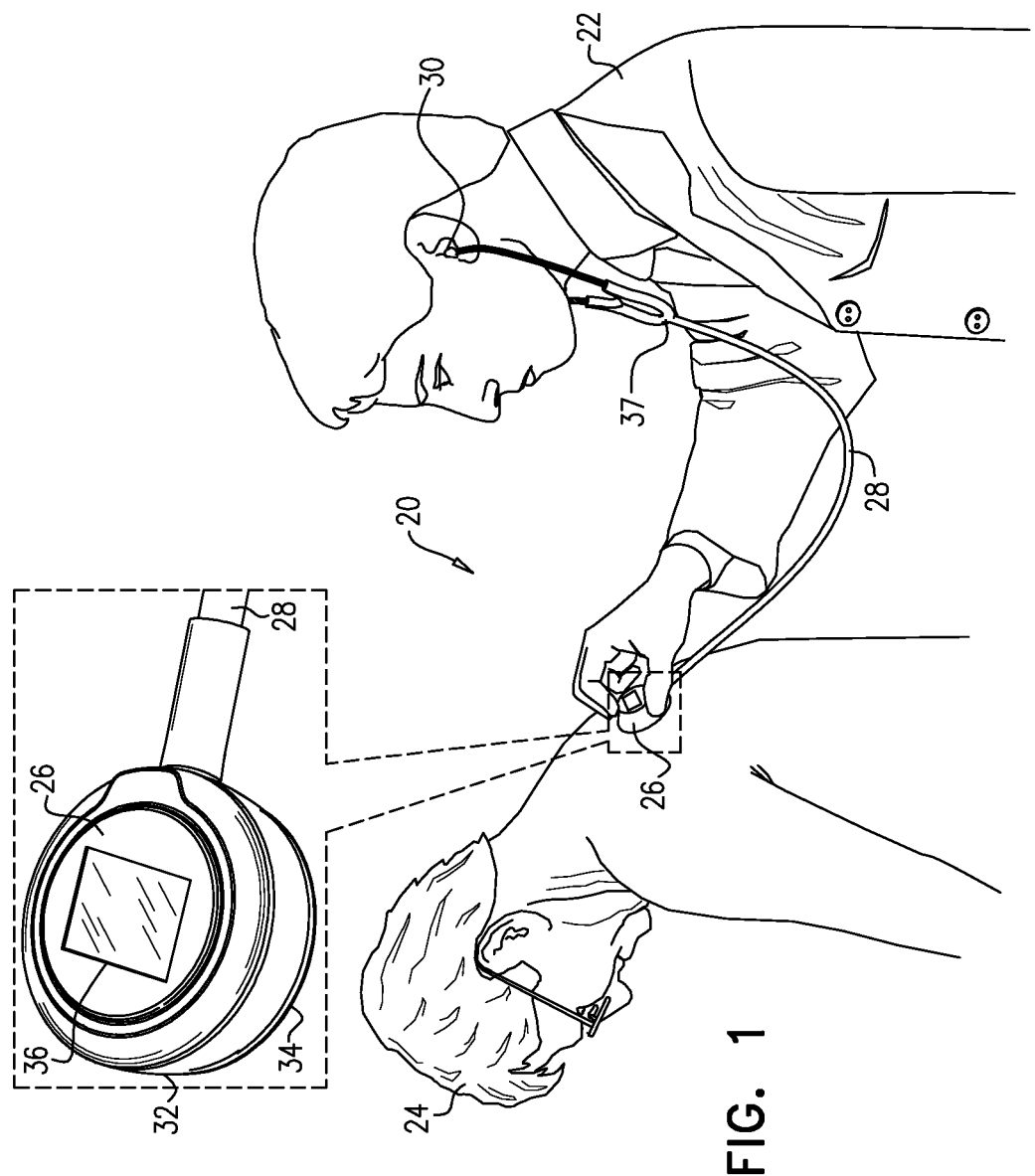
FIG. 1 is a schematic pictorial illustration showing an electronic stethoscope in clinical use, in accordance with an embodiment of the invention.

The stethoscope is generally the first tool that the medical practitioner deploys in attempting to diagnose conditions of the circulatory and respiratory systems. Stethoscopes that are known in the art, however, including electronic stethoscopes, are limited by the user's auditory capabilities and diagnostic skills. Signals available at the body surface due to physiological activity contain a wealth of diagnostic information that is not exploited either by traditional auscultation or by electronic stethoscopes that are known in the art.

Embodiments of the present invention that are described herein provide medical devices that offer functionalities of electronic stethoscopes with enhanced diagnostic capabilities and ease of use. The devices described below include a case, whose front surface is brought into contact with the body of a living subject. The case contains a microphone, which senses acoustic waves emitted from the body, as well as a proximity sensor, which outputs a proximity signal indicative of contact between the front surface of the case and the body. At least one speaker, in or connected to the case, outputs audible sounds. Typically (although not necessarily), the audible sounds are conveyed to earphones, which are inserted in the ears of an operator, for example by acoustic tubes connecting the speaker to the earphones or by integrating a pair of speakers into the earphones.

Based on the proximity signal, processing circuitry, which may be contained in the case, detects, that the front surface of the case is in contact with the body. In response to the detected contact, the circuitry processes acoustic signals output by the microphone so as to generate an audio output, which is conveyed to the speaker or speakers. This sort of contact sensing is useful in ensuring good-quality contact between the front surface of the case and the body. The processing circuitry may output an indication of the contact quality that is detected in this manner to an operator of the device.

Additionally or alternatively, the processing circuitry can make use of the proximity signal in reducing power consumption, by powering down one or more components of the device when the proximity signal indicates that the front surface is not in contact with the body, and powering them up only when the proximity signal indicates that contact has been made between the front surface of the case and the body. Further additionally or alternatively, for purposes of power saving, the processing circuitry may detect that the earphones of the stethoscope have been spread apart—indicating that a practitioner is preparing to use the device—and may power up components of the device in response thereto. These measures are useful not only in conserving power, but also in relieving the practitioner of the need to continually switch the device on and off.

In some embodiments, the proximity sensor comprises one or more emitters, which emit optical radiation toward the body, and a detector, which senses the optical radiation reflected from the body and outputs the proximity signal on this basis. When the emitter or emitters output appropriate wavelengths, for example in the near-infrared range, the processing circuitry can use the output of the detector to measure the level of oxygen saturation in the subject's blood, so that the device functions as a pulse oximeter, in addition to it audio functionality.

In the embodiments that are described below, the head of the stethoscope also contains a motion sensor, which outputs a motion signal in response to motion of the front surface of the case. The processing circuitry may process this motion signal in order to detect respiratory motion, and thus extract the respiratory cycle of the subject. Additionally or alternatively, the front surface of the case may comprise a membrane, which vibrates in response to the acoustic waves emitted from the body. The motion sensor senses this vibratory motion, and the processing circuitry can then process the motion signal in order to detect an infrasonic component of the acoustic waves emitted from the body.

Further additionally or alternatively, the processing circuitry may process acoustic signals from the microphone and/or the motion sensor so as to generate a frequency-stretched audio output, in which infrasonic frequency components of the acoustic signal are shifted to audible frequencies while preserving the periodicity of the periodic physiological activity. This frequency-stretched audio output is conveyed to the speaker or speakers.

In some embodiments, the device comprises a touch-sensitive display screen on the rear surface of the case. The processing circuitry can present a user interface on the display screen and receive inputs from the operator of the device via the display screen. These inputs may indicate, for example, a processing mode, such as a cardiac or respiratory signal processing mode, and/or a frequency shift to be applied in processing of the acoustic signals from the microphone. Additionally or alternatively, the processing circuitry may compute, based on the acoustic signals, an acoustic signature, and may render this acoustic signature to the display screen. The acoustic signature typically comprises a graphical representation of the spectral distribution of the energy of the acoustic waves over a period of physiological activity, such as a heart cycle or respiration cycle.

In the embodiments that are shown in the figures and described below, the features described above, as well as other inventive aspects of the present invention, are shown in combination, by way of example, in the context of a particular design of an electronic stethoscope. Although this combination of features in a single device is advantageous, in terms of the range of capabilities and benefits offered to the operator of the device, those skilled in the art will understand that subsets of these features, including individual features among those described above, may be incorporated in an electronic stethoscope or other medical device, independently of the remaining features. All such individual features and combinations thereof are considered to be within the scope of the present invention, even if not enumerated specifically in the present description.

System Description

FIG. 1 is a schematic pictorial illustration showing the use of a digital stethoscope 20, in accordance with an embodiment of the invention. A practitioner 22 brings a head 26 of stethoscope 20 into contact with the body of a patient 24. Processing circuitry in head 26 outputs an audio signal via a cable 28 extending from head 26 to one or more speakers, which are typically integrated in or acoustically coupled to earphones 30. The two earphones 30 are joined at a spring-loaded junction 37, and thus open apart and fit into the practitioner's ears as would the earphones of a conventional stethoscope.

As shown in the inset, head 26 comprises a case 32, which contains an acoustic transducer, such as a suitable microphone 34, which contacts the body of patient 24 and thus senses acoustic waves emitted from the body. Microphone 34 may be of any suitable type that is known in the art, for example a piezoelectric sensor or a MEMS (micro-electromechanical systems) microphone, which is sensitive not only to audible frequencies, but also to infrasonic frequencies going down to about 5 Hz. On the other side of head 26, a user interface, such as a touch-sensitive display 36, enables practitioner 22 to control the functions of stethoscope 20 and displays data, such as acoustic signatures of heart and/or breath sounds sensed by microphone 34. Other components and functions of head 26 are described with reference to the figures that follow.

Figure 2:
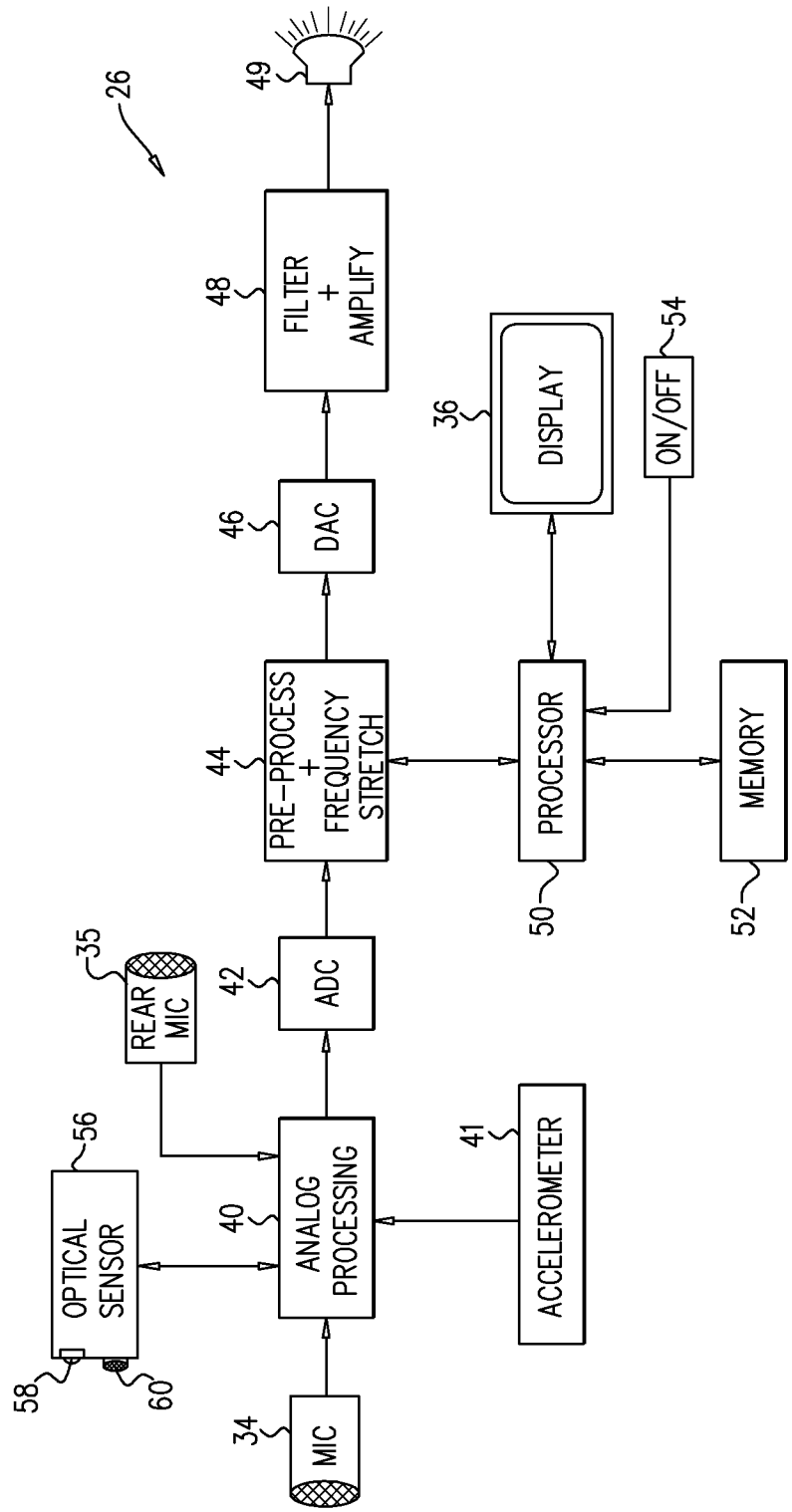
FIG. 2 is a block diagram that schematically shows elements of an electronic stethoscope, in accordance with an embodiment of the invention.
Figure 3:
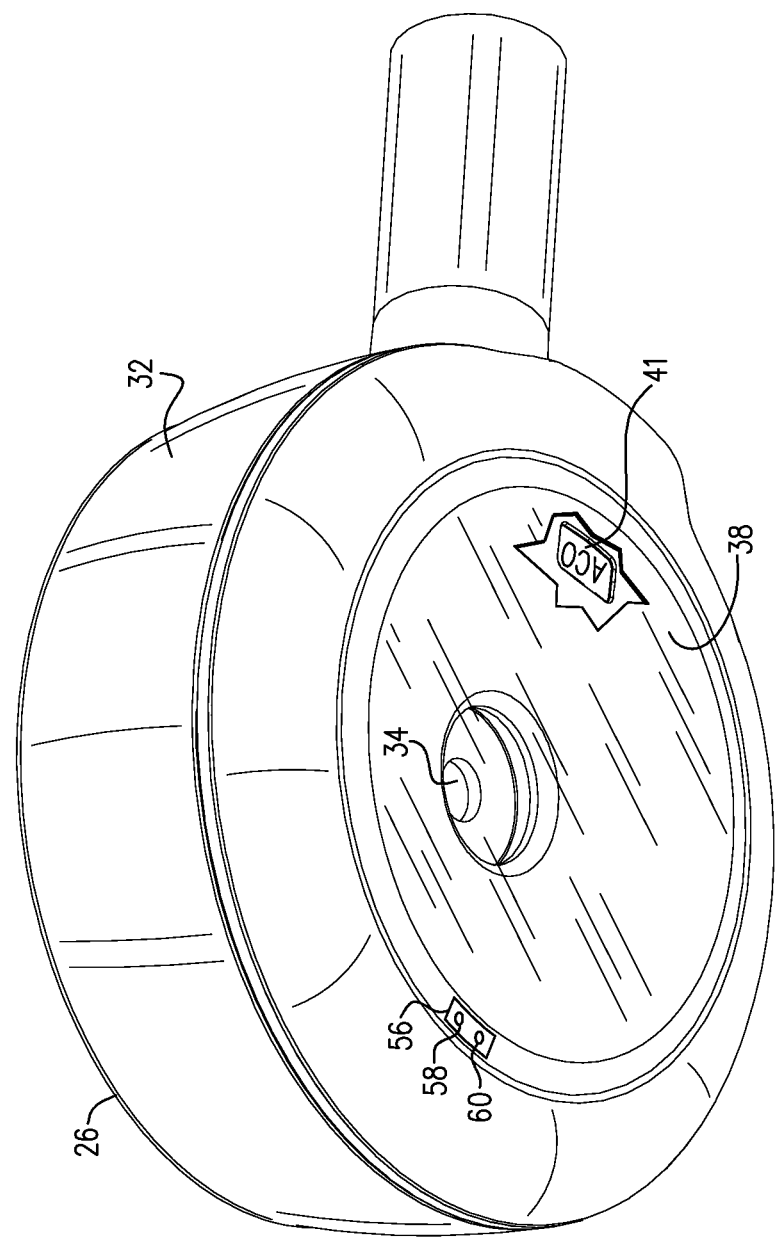
FIG. 3 is a schematic pictorial illustration showing details of the head of an electronic stethoscope, in accordance with an embodiment of the invention.

Reference is now made to FIGS. 2 and 3, which schematically illustrate functional elements of stethoscope 20, in accordance with an embodiment of the invention. FIG. 2 is a block diagram, while FIG. 3 is a pictorial detail view of head 26 of stethoscope 20. In the present embodiment, the elements shown in FIG. 2 are assumed to be contained inside head 26, within case 32, with the possible exception of one or more speakers 49 (and possibly an on/off switch 54, as explained below). Alternatively, however, certain components may be housed in other parts of stethoscope 20 or in an external processing unit.

The front surface of head 26, which is brought into contact with the patient's body, comprises a membrane 38. Microphone 34 is typically mounted at the center of this membrane. Acoustic waves from the body impinge on membrane 38, causing the membrane to deflect. The deflection of membrane 38 is translated into an acoustic signal, which is processed, as described in detail below, to generate an audio output, which is played via speaker 49 to earphones 30 in the example shown in FIG. 1. Features of membrane 38 and microphone 34 are described further in the above-mentioned PCT International Publication WO 2017/141165.

An analog front end 40 performs analog processing functions, including filtering, buffering and amplification of the electrical signals output by microphone 34. Optionally, head 26 also contains a rear microphone 35, in a location that is physically separated from membrane 38, which captures background sounds. These background sounds are subtracted from the signals from microphone 34. The subtraction may be carried out either in analog front end 40 or digitally, for example by adaptive filtering in either the time or frequency domain, following digitization of the signals, as described below.

Head 26 also comprises an inertial sensor, such as an integrated circuit accelerometer 41, which measures motion of head 26 and low-frequency vibrations of membrane 38. Analog front end 40 processes the signals output by the inertial sensor, as well. Accelerometer 41 is typically disposed on the inner side of membrane 38, and may serve at least two functions: both detecting movement of the chest caused by respiration, which causes head 26 to move cyclically at the respiration frequency, and detecting deflections of membrane 38 at vibrational frequencies below the minimum frequency that is detectable by microphone 34. The accelerometer and microphone thus complement one another, in that the accelerometer detects sound at very low frequencies that are not detectable by the microphone, and the microphone detects sound at higher frequencies that are not detectable by the accelerometer.

An analog/digital converter (ADC) 42 digitizes the acoustic and inertial signals, and possibly also other analog inputs. For purposes of audio enhancement and analysis, a digital preprocessing circuit 44 transforms the digitized signals to the frequency domain, for example by computing a short-time Fourier transform (STFT) over successive time windows of the signals. In addition, circuit 44 can perform digital filtering functions, such as noise suppression, and "frequency stretching": shifting infrasonic frequency components to the audible frequency range, as described further hereinbelow. Following these filtering and frequency stretching steps, circuit 44 converts the frequency-domain samples back to the time domain. For these purposes, circuit 44 typically comprises digital processing logic, which may be hard-wired or programmable; but alternatively, at least some of the functions of circuit 44 may be carried out on a programmable processor under the control of software or firmware.

A digital/analog converter (DAC) 46 converts the stream of processed time-domain samples to analog form. In this manner, practitioner can choose to hear audible versions of the infrasonic frequency components captured by microphone 34 and accelerometer 41, following frequency-stretching to the audible range, in addition to or instead of the audible frequency components themselves that are captured by the microphone. An analog output circuit 48 filters and amplifies the analog signal to generate an electrical audio output to speaker or speakers 49.

A programmable processor 50 receives the stream of samples—in either the time domain or the frequency domain, or both—from digital preprocessing circuit 44. Processor 50 is coupled to a memory 52, which typically comprises non-volatile memory, such as flash memory, containing software or firmware to control the operations of processor 50. In addition, memory 52 typically comprises volatile random-access memory (RAM), which is used by processor 50 to store the digital samples received from circuit 44, as well as processing results.

Based on the digitized samples, processor 50 can compute acoustic signatures, representing the spectral distribution of the energy of the acoustic waves over the period of the cardiac or respiratory cycle, as described further hereinbelow. Processor 50 renders a graphical representation of the acoustic signature to display 36 and/or outputs the signature information via a communication link (not shown). In addition, processor 50 may receive and carry out user instructions, for example in response to finger gestures on the touch screen of display 36. These functions of display 36 are illustrated and described further hereinbelow with reference to FIGS. 4 and 5.

The processing components shown FIG. 2, including analog front end 40, ADC 42, digital preprocessing circuit 44, DAC 46, analog output circuit 48, processor 50 and memory 52, are collectively and individually referred to herein as "processing circuitry." These components are typically implemented in integrated circuits, as are known in the art, which are mounted together on a printed circuit board within case 32. Alternatively, other implementations of these functional components will be apparent to those skilled in the art after reading the present description and are considered to be within the scope of the present invention. Although FIG. 2 shows a certain arrangement of functional blocks for the sake of conceptual clarity, the functions of at least some of these blocks may be combined into a single integrated circuit chip or, alternatively, split among multiple chips.

Typically (although not necessarily), the functions of stethoscope 20, and specifically of the processing circuitry described above, are powered by a battery (not shown). In order to conserve battery power, it is desirable that at least some of the components of the processing circuitry be powered down automatically when not in use, and then powered up automatically when needed, without requiring practitioner 22 to operate an on/off switch. For this purpose, stethoscope 20 comprises an on/off sensor 54, which detects an action made by practitioner in preparation for applying head 26 to patient 24. For example, sensor 54 may comprise an electro-mechanical component, which is connected to junction 37 (FIG. 1) and outputs a signal when earphones 30 are spread apart. In response to this signal, processor 50 powers up the processing circuitry. When the earphones are released, the processing circuitry may be powered down.

Additionally or alternatively, head 26 comprises a proximity sensor 56, which outputs a proximity signal indicative of contact between the front surface of case 32 and the patient's body. For example, proximity sensor 56 may be an optical sensor, comprising one or more emitters 58, which emit optical radiation toward the body, and a detector 60, which senses the optical radiation reflected from the body. Detector 60 thus outputs a signal (referred to herein as a "proximity signal") that is indicative of the proximity of sensor 56 to the patient's skin. Alternatively or additionally, head 26 may comprise other types of proximity sensors, such as a strain gauge or other pressure sensor, which measures the pressure of head 26 against the patient's body.

Based on the signal from detector 60, processor 50 is able to determine whether or not head 26 is in contact with the patient's body. Thus, stethoscope 20 may automatically convey the processed audio output to speaker 49 (and from there to earphones 30) only when the front surface of head 26 is in proper contact with the body. Processor 50 may otherwise power down certain components of the stethoscope when the signal from detector 60 indicates that the front surface of head 26 is not in contact with the body, and may then power up the components when contact is made. This functionality may be instead of or in addition to that of on/off sensor 54.

As another option, processor 50 may assess, based on intensity and/or other features of the reflected light sensed by detector 60, the quality of the contact between the front surface of head 26 and the body. Processor 50 may thus be able to measure whether practitioner 22 is pressing head 26 against the patient's body with sufficient force, or perhaps too much force, and to output an indication of the detected quality to practitioner 22. For example, processor 50 may render a graphical and/or alphanumeric output to display 36, indicating, for example, that the contact between head 26 and the patient's skin is too weak, or possibly too strong.

In addition, in one embodiment, processor 50 processes the signals output by detector 60 in order to measure the level of oxygen saturation in the blood of patient 24. For this purpose, emitter 58 typically emits optical radiation at appropriate wavelengths, such as an infrared wavelength and a visible wavelength, for example at 940 nm and 660 nm, as is known in the art. Emitter 58 may comprise a pair of suitable light-emitting diodes for this purpose. Emitter 58 emits the two wavelengths in sequential alternation, and processor 50 compares the signals output by detector 60 in response to the two wavelengths in order to calculate the approximate oxygen saturation level. Processor 50 outputs an indication of the saturation level to display 36, along with other data outputs and controls.

Modes of Operation

Figure 4:
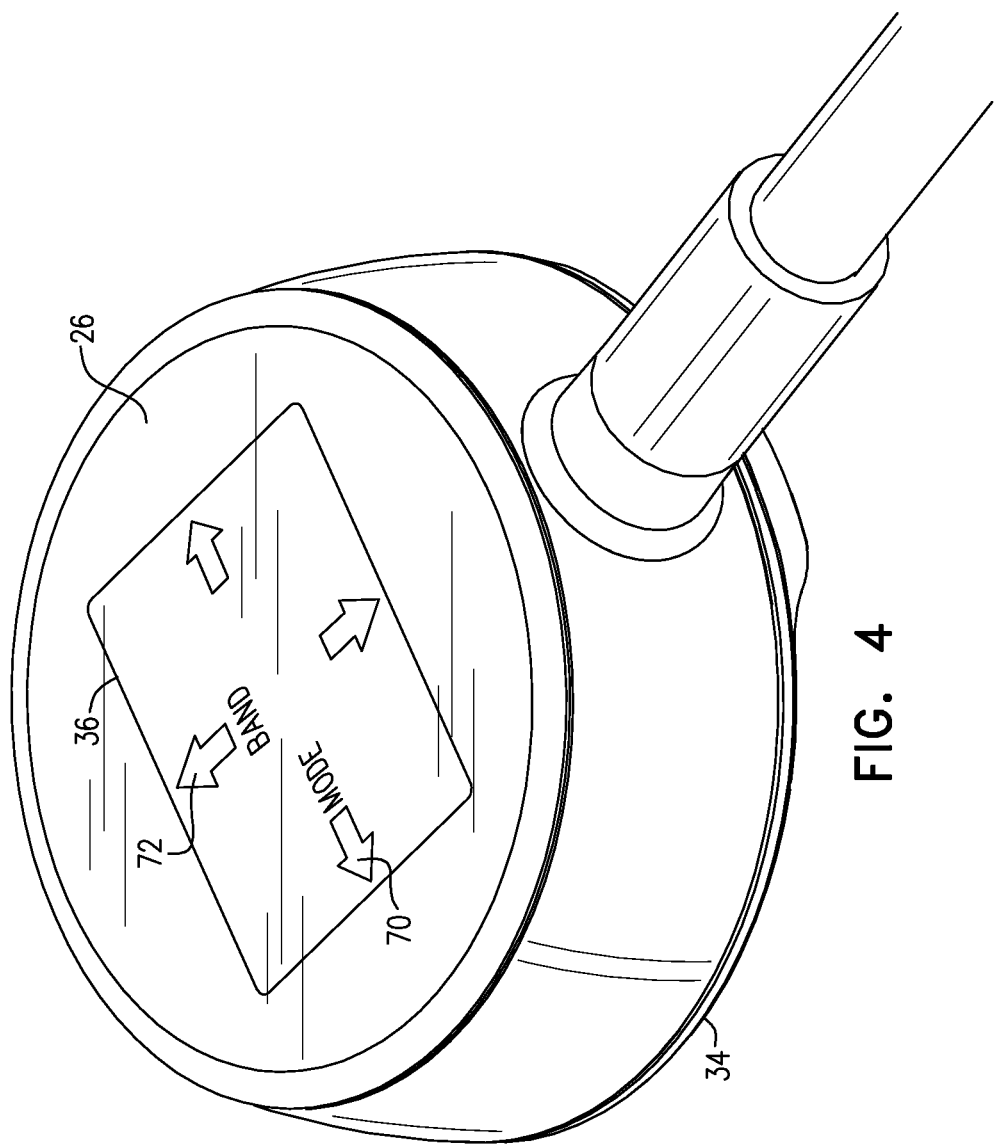
FIGS. 4 and 5 are schematic pictorial illustrations showing operation of an interactive display on the head of an electronic stethoscope, in accordance with an embodiment of the invention.

FIG. 4 is a schematic pictorial illustration of stethoscope head 26, showing elements of a user interface presented by processor 50 on touch-sensitive display 36, in accordance with an embodiment of the invention. The user interface includes a mode selection control 70 and a band selection control 72, which are operated by finger gestures made by practitioner 22 against the display screen. For example, the practitioner may swipe his finger left or right on the screen to change the processing mode, and may swipe his finger up or down to choose a frequency shift to be applied in processing of the acoustic signals captured by head 26. The processing mode can be selected for example, to be a cardiac signal processing mode or a respiratory signal processing mode. Band selection control 72 allows the user to turn frequency stretching on and off, in order to shift infrasonic signals to the audible range, as well as to choose the degree of stretching to be applied. In addition, display 36 can present other controls and data outputs, as will be apparent to those skilled in the art after reading the present description.

As explained above (in reference to FIG. 2), analog front end 40 receives the electrical signals output by microphones 34 and 35 and by accelerometer 41, and ADC 42 digitizes the signals. The time-domain digital samples are input to digital preprocessing circuit 44, which performs preprocessing functions that may include subtracting background audio signals captured by microphone 35. Circuit 44 then transforms the digitized signals to the frequency domain, using a short-time Fourier transform (STFT), for example.

To extend the spectrum down to the low infrasonic range, the vibrational signals captured by accelerometer 41 may similarly be transformed and incorporated into the spectrum together with the (background-subtracted) signals from microphone 34. In processing the accelerometer output, circuit 44 typically applies appropriate frequency filters to this output, such as to differentiate chest movements (which typically have a frequency of 0.1-0.2 Hz) from deflections of membrane 38 having higher or lower frequencies. The membrane-deflection portion of the accelerometer output can then be integrated with the output from microphone 34. Processor 50 can analyze the chest-movement portion of the accelerometer output, such as to identify the various stages in the respiratory cycle of the subject.

Formally, the STFT F(m,k) of the time-domain audio signal f[n], is computed by applying the formula:

$$F(m,k) = \Sigma_n f[n] * w[n-m] * e^{-jkn}$$

Here m and k are both discrete variables (m being the time variable and k being the frequency variable), and w[n] is a suitable window function, such as a Hamming, Gaussian, or Hann window function.

To stretch the infrasonic signals into the audible range, circuit 44 interpolates the frequency spectrum F(m,k) in the frequency domain by a factor R in order to yield interpolated spectrum $F_r(m,k)$, in which the infrasonic components are shifted to audible frequencies. Generally speaking, R may take any rational value, but typical values of R are in the range between 2 and 20, in order to shift infrasonic frequency components to the low end of the audible range. Assuming that the infrasonic frequency components sensed by microphone 34 have frequencies extending at least down to 5 Hz, and circuit 44 will use a value of R such that the infrasonic frequency component at 5 Hz will be shifted to a frequency of at least 20 Hz.

Different values of R can be used depending upon whether practitioner 22 wishes to hear respiratory or cardiac sounds. For example, respiratory sounds typically fall within the range of 12-2000 Hz, which can be shifted to the audible range of 24-4000 Hz by setting R=2. As another example, heart sounds typically fall within the range of 5-200 Hz, which can be shifted to the audible range of 40-1600 Hz by setting R=8. Optionally, practitioner 22 may select the value of R (for example, toggling between preset values for different types of physiological activity) by entering an appropriate user input to stethoscope 20, using controls 70 and 72 on the touch screen of display 36, for example, as illustrated in FIG. 4.

Stretching the frequency content of this acoustic signal, so as to slow down or accelerate the temporal evolution of a sound without altering its time period, requires an explicit separation of temporal and spectral information. To carry out the required time domain preservation, digital preprocessing circuit 44 first computes $f_r[n]$, the inverse STFT of $F_r(m,k)$, as given by the formula:

$$f_r[n] = \frac{1}{2\pi} \sum_m \sum_k F_r(m,k) * e^{jkn}$$

Circuit 44 then decimates the sequence of time-domain samples $f_r[n]$ by the same factor R as was used in interpolation of the frequency spectrum to give a frequency-stretched signal $f_s[n]$, which has the same number of samples, and hence the same periodicity, as the original f[n], but is stretched to higher frequencies. (This decimation is equivalent to replaying the frequency-shifted sequence of time-domain samples $f_r[n]$ at R times the original sample rate.) DAC 46 converts $f_s[n]$ to analog form, and analog output circuit 48 amplifies and inputs this signal to speaker or speakers 49.

Computation and Display of Acoustic Signatures

Figure 5:
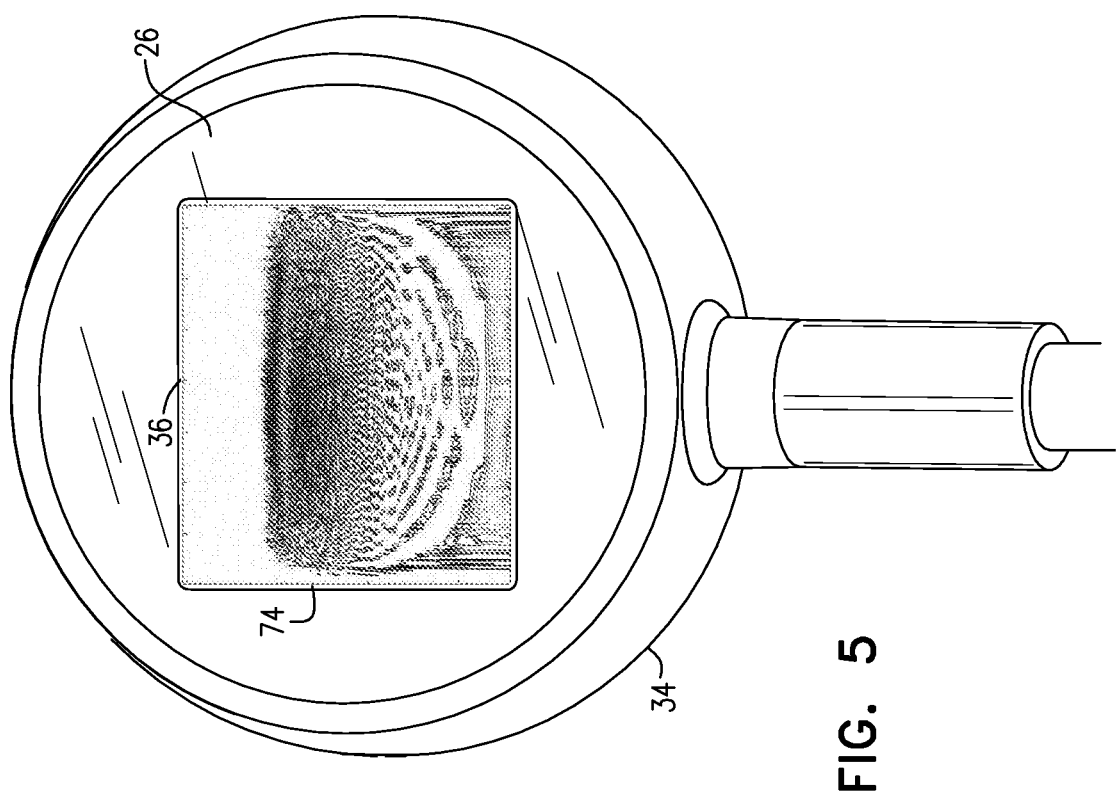

FIG. 5 is a schematic pictorial illustration of stethoscope head 26, showing an acoustic signature 74 on display 36, in accordance with an embodiment of the invention. Acoustic signature 74 is a graphical representation of the spectral distribution of the energy of the acoustic waves over a period of physiological activity. In the example shown in FIG. 5, signature 74 is derived from chest sounds (including infrasonic components) due to respiratory activity, and is thus indicative of the patient's respiratory patterns. Signature 74, by way of example, is indicative of chronic obstructive pulmonary disease (COPD). Alternatively, practitioner 22 may select the operating mode of stethoscope 20, using mode selection control 70 on the touch screen interface of display 36, for example, to obtain and present an acoustic signature of the patient's cardiac activity.

As explained in detail in the above-mentioned U.S. patent application Ser. No. 15/953,502, acoustic signature 74 is based on the autocorrelation spectrum of acoustic signals received from microphone 34 over the period of a physiological activity of interest, such as the autocorrelation of heart sounds over the cardiac cycle or breath sounds over the respiratory cycle. For this purpose, for example, processor 50 can detect the respiratory motion of the patient's thorax using the output of accelerometer 41 and thus extract the period of the patient's respiratory activity. Additionally or alternatively, the period of the activity, based on the digitized signal x(n) from microphone 34 or accelerometer 41, can itself be computed by finding and analyzing significant peaks in the autocorrelation function.

To compute the acoustic signature of the respiratory activity, processor 50 builds a two-dimensional (2D) autocorrelation matrix based on the digitized samples of the electrical signals from microphone 34 and possibly accelerometer 41, and then applies an appropriate transform to the 2D autocorrelation matrix to generate a matrix representation of the spectral (frequency) distribution of the energy of the acoustic waves over the respiratory period. This matrix constitutes the spectral signature of the patient's cardiac or respiratory activity.

Processor 50 can then render a graphical representation of this signature to display 36 or to a separate, external display (not shown). Typically, this graphical representation comprises a plot having a frequency axis and a time axis, which together define a time-frequency plane. The value of the energy is presented in the plot at each point in the time-frequency plane. Signature 74, as shown in FIG. 5, is one example of such a graphical representation, while other examples are shown in the above-mentioned U.S. patent application Ser. No. 15/953,502. These acoustic signatures can thus assist the practitioner in making fast, accurate diagnoses and assessing changes in the patient's condition thereafter.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical device, comprising:
    a case having a front surface that is configured to be brought into contact with a body of the living subject, wherein the front surface comprises a membrane which is configured to vibrate in response to acoustic waves emitted from the body;
    a microphone which is contained in the case and configured to sense the acoustic waves emitted from the body and to output an acoustic signal in response thereto;
    a proximity sensor which is configured to output a proximity signal indicative of contact between the front surface and the body;
    at least one speaker configured to output audible sounds;
    a motion sensor which is contained in the case and is configured to configured to sense the motion of the membrane and output a motion signal in response to the motion, and
    processing circuitry which is configured to
        receive the output proximity signal,
        detect, in response to receiving the proximity signal, that the front surface is in contact with the body, and,
        in response to the detected contact, process the acoustic signal so as to generate an audio output and to convey the audio output to the at least one speaker, and
        process the motion signal in order to detect an infrasonic component of the acoustic waves;
    wherein the proximity sensor comprises at least one emitter which is configured to emit optical radiation, including infrared radiation, toward the body, and a detector which is configured to sense the optical radiation reflected from the body,
    wherein the proximity signal indicative of contact that is output to the processing circuitry is responsive to the reflected radiation sensed by the detector, and the processing circuitry is also configured to measure a level of oxygen saturation in blood of the subject responsively to the reflected radiation sensed by the detector.

2. The device according to claim 1, wherein the processing circuitry is further configured to process the motion signal in order to detect a respiratory cycle of the subject.

3. The device according to claim 1, wherein the processing circuitry is further configured to process the acoustic signal so as to generate a frequency-stretched audio output in which infrasonic frequency components of the acoustic signal are shifted to audible frequencies while preserving the periodicity of the periodic physiological activity, and to convey the frequency-stretched audio output to the at least one speaker.

4. The device according to claim 1, wherein the processing circuitry is further configured to power down one or more components of the device when the proximity signal indicates that the front surface is not in contact with the body, and to power up the one or more components when the proximity signal indicates that the front surface is in contact with the body.

5. The device according to claim 1, and further comprising a pair of earphones which are configured to be inserted in respective ears of an operator of the device and to convey the audible sounds to the ears.

6. The device according to claim 5, wherein the processing circuitry is further configured to detect that the earphones have been spread apart and to power up one or more components of the device in response thereto.

7. The device according to claim 1, wherein the processing circuitry is further configured to detect, in response to the proximity signal, a quality of the contact between the front surface and the body, and to output an indication of the detected quality to an operator of the device.

8. The device according to claim 1, wherein the case has a rear surface opposite the front surface, and wherein the device further comprises a touch-sensitive display screen mounted on the rear surface of the case.

9. The device according to claim 8, wherein the processing circuitry is further configured to present a user interface on the display screen and to receive an input from an operator of the device via the display screen indicating a processing mode and frequency shift to be applied in processing of the acoustic signal.

10. The device according to claim 9, wherein the processing mode is selected from a group of processing modes consisting of a cardiac signal processing mode and a respiratory signal processing mode.

11. The device according to claim 8, wherein the processing circuitry is further configured to compute an acoustic signature responsively to the acoustic signal, the acoustic signature comprising a graphical representation of a spectral distribution of an energy of the acoustic waves over a period of physiological activity, and to render the acoustic signature to the display screen.

12. The device according to claim 11, wherein the processing circuitry is further configured to compute respective autocorrelations of the acoustic signal fora plurality of different times within a period of the physiological activity, to transform the respective autocorrelations to a frequency domain, and to render the acoustic signature to the display screen responsively to the transformed autocorrelations.

13. The device according to claim 11, wherein the spectral distribution includes the energy at infrasonic frequencies.

14. The device according to claim 11, wherein the graphical representation comprises a plot having a frequency axis and a time axis defining a time-frequency plane and presenting a value of the energy at each point in the time-frequency plane.

15. A method for medical diagnosis, comprising:
receiving, from a microphone in a case having a front surface comprising a membrane that is brought into contact with a body of a living subject, an acoustic signal in response to acoustic waves emitted from the body;
emitting optical infrared radiation toward the body, sensing the infrared optical radiation reflected from the body, and outputting in response to the sensed reflected radiation a proximity signal indicative of contact between the front surface of the case and the body;
sensing a movement associated with the body using a motion sensor which is contained in the case, wherein the movement comprises a vibration of the membrane in response to the acoustic waves emitting from the body and outputting a motion signal in response to motion of the front surface;
receiving the proximity signal indicative of contact between the front surface of the case and the body;
detecting, in response to the proximity signal, that the front surface is in contact with the body; and
in response to the detected contact, processing the acoustic signal so as to generate and convey an audio output to at least one speaker, and
processing the motion signal in order to detect an infrasonic component of the acoustic waves;
wherein the method further comprises measuring a level of oxygen saturation in blood of the subject responsively to the sensed reflected radiation.

16. The method according to claim 13, wherein the movement is due to respiration of the subject, and wherein the method comprises processing the motion signal in order to detect a respiratory cycle of the subject.

17. The method according to claim 15, wherein processing the acoustic signal further comprises generating a frequency-stretched audio output in which infrasonic frequency components of the acoustic signal are shifted to audible frequencies while preserving the periodicity of the periodic physiological activity, and conveying the frequency-stretched audio output to the at least one speaker.

18. The method according to claim 15, and further comprising powering down one or more components that are used in processing the acoustic signal when the proximity signal indicates that the front surface is not in contact with the body, and powering up the one or more components when the proximity signal indicates that the front surface is in contact with the body.

19. The method according to claim 15, wherein processing the acoustic signal further comprises conveying the audible sounds to a pair of earphones configured for insertion in respective ears of an operator.

20. The method according to claim 19, and further comprising detecting that the earphones have been spread apart, and powering up one or more components that are used in processing the acoustic signal in response thereto.

21. The method according to claim 15, and further comprising detecting, in response to the proximity signal, a quality of the contact between the front surface and the body, and outputting an indication of the detected quality.

22. The method according to claim 15, wherein the case has a rear surface opposite the front surface, and wherein the method further comprises presenting information on a touch-sensitive display screen mounted on the rear surface of the case.

23. The method according to claim 22, wherein presenting the information comprises presenting a user interface on the display screen and receiving an input via the display screen indicating a processing mode and frequency shift to be applied in processing of the acoustic signal.

24. The method according to claim 23, wherein the processing mode is selected from a group of processing modes consisting of a cardiac signal processing mode and a respiratory signal processing mode.

25. The method according to claim 22, wherein processing the acoustic signal comprises computing an acoustic signature, comprising a graphical representation of a spectral distribution of an energy of the acoustic waves over a period of physiological activity, and wherein presenting the information comprises rendering the acoustic signature to the display screen.

26. The method according to claim 25, wherein computing the acoustic signature comprises computing respective autocorrelations of the acoustic signal for a plurality of different times within a period of the physiological activity, transforming the respective autocorrelations to a frequency domain, and rendering the acoustic signature to the display screen responsively to the transformed autocorrelations.

27. The method according to claim 25, wherein the spectral distribution includes the energy at infrasonic frequencies.

28. The method according to claim 25, wherein the graphical representation comprises a plot having a frequency axis and a time axis defining a time-frequency plane and presenting a value of the energy at each point in the time-frequency plane.

* * * * *